US00PP29130P3

(12) United States Plant Patent
Svenson

(10) Patent No.: US PP29,130 P3
(45) Date of Patent: Mar. 20, 2018

(54) ***PIERIS* PLANT NAMED 'CABERNET'**

(50) Latin Name: *Pieris japonica*
Varietal Denomination: Cabernet

(71) Applicant: Sven E. Svenson, Salem, OR (US)

(72) Inventor: Sven E. Svenson, Salem, OR (US)

( * ) Notice: Subject to any disclaimer, the term of this patent is extended or adjusted under 35 U.S.C. 154(b) by 37 days.

(21) Appl. No.: 14/999,743

(22) Filed: Jun. 22, 2016

(65) Prior Publication Data

US 2016/0381846 P1 Dec. 29, 2016

Related U.S. Application Data

(60) Provisional application No. 62/231,056, filed on Jun. 23, 2015.

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Keith O Robinson
(74) *Attorney, Agent, or Firm* — C. A. Whealy

(57) ABSTRACT

A new and distinct cultivar of *Pieris* plant named 'Cabernet', characterized by its compact plant habit; freely branching habit; leaves that are initially greyed red in color and with development become green in color; inflorescences that are horizontal to drooping in aspect; relatively late flowering response; numerous deep red purple-colored flowers; and good garden performance.

2 Drawing Sheets

Botanical designation: *Pieris japonica.*
Cultivar denomination: 'CABERNET'.

BACKGROUND OF THE INVENTION

The present Invention relates to a new and distinct cultivar of *Pieris* plant, botanically known as *Pieris japonica*, and hereinafter referred to by the name 'Cabernet'.

The new *Pieris* plant is a product of a planned breeding program conducted by the Inventor in Hopewell, Oreg. The objective of the breeding program is to develop new compact and freely-branching *Pieris* plants with stable and attractive flower color and good garden performance.

The new *Pieris* plant originated from a cross-pollination made by the Inventor in March, 1997, in Hopewell, Oreg., of *Pieris japonica* var. *japonica* 'Reversal', not patented, as the female, or seed, parent with the *Pieris japonica* 'Valley Valentine', not patented, as the male, or pollen, parent. The new *Pieris* plant was discovered and selected by the Inventor as a single flowering plant within the progeny of the stated cross-pollination in a controlled outdoor nursery environment in Hopewell, Oreg. in early March, 2002.

Asexual reproduction of the new *Pieris* plant by cuttings propagated in a controlled environment in Hopewell, Oreg. since 2002 has shown that the unique features of this new *Pieris* plant are stable and reproduced true to type in successive generations.

SUMMARY OF THE INVENTION

Plants of the new *Pieris* have not been observed under all possible combinations of environmental conditions and cultural practices. The phenotype may vary somewhat with variations in environmental conditions such as temperature, length of growing season and/or light intensity without, however, any variance in genotype. The following traits have been repeatedly observed and are determined to be the unique characteristics of 'Cabernet'. These characteristics in combination distinguish 'Cabernet' as a new and distinct *Pieris* plant:

1. Compact plant habit.
2. Freely branching habit.
3. Leaves that are initially greyed red in color and with development become green in color.
4. Inflorescences that are horizontal to drooping in aspect.
5. Relatively late flowering response.
6. Numerous deep red purple-colored flowers.
7. Good garden performance.

Plants of the new *Pieris* differ primarily from plants of the female parent, 'Reversal', in the following characteristics:

1. Plants of the new *Pieris* are more freely branching than plants of 'Reversal'.
2. Plants of the new *Pieris* retain leaves for a longer period of time than plants of 'Reversal'.
3. Developing leaves of plants of the new *Pieris* are greyed red in color whereas developing leaves of plants of 'Reversal' are yellow green in color.
4. Inflorescences of plants of the new *Pieris* are more upright than inflorescences of plants of 'Reversal'.
5. Plants of the new *Pieris* flower later than plants of 'Reversal'.
6. Plants of the new *Pieris* are more freely flowering than plants of 'Reversal'.
7. Flower buds of plants of the new *Pieris* are deep greyed purple in color whereas flower buds of plants of 'Reversal' are red purple in color.

Plants of the new *Pieris* differ primarily from plants of the male parent, 'Valley Valentine', in the following characteristics:

1. Developing leaves of plants of the new *Pieris* are greyed red in color whereas developing leaves of plants of 'Valley Valentine' are greyed orange in color.

2. Flower buds of plants of the new *Pieris* are deep greyed purple in color whereas flower buds of plants of 'Valley Valentine' are red purple in color.
3. Sepals, peduncles and pedicels of plants of the new *Pieris* are red in color whereas sepals, peduncles and pedicels of plants of 'Valley Valentine' are greyed purple in color.

Plants of the new *Pieris* can be compared to the plants of the *Pieris japonica* 'Passion', disclosed in U.S. Plant Pat. No. 19,319. In side-by-side comparisons conducted in Hopewell, Oreg., plants of the new *Pieris* differed from plants of 'Passion' in the following characteristics:

1. Developing leaves of plants of the new *Pieris* were greyed red in color whereas developing leaves of plants of 'Passion' were yellow green in color.
2. Leaves of plants of the new *Pieris* were broader than leaves of plants of 'Passion'.
3. Plants of the new *Pieris* flowered later and flowers lasted for a longer period of time than plants of 'Passion'.
4. Inflorescences of plants of the new *Pieris* were broader and longer than inflorescences of plants of 'Passion'.
5. Sepals, peduncles and pedicels of plants of the new *Pieris* were red purple in color whereas sepals, peduncles and pedicels of plants of 'Passion' were greyed purple to brown in color.

BRIEF DESCRIPTION OF THE PHOTOGRAPHS

The accompanying colored photographs illustrate the overall appearance of the new *Pieris* plant showing the colors as true as it is reasonably possible to obtain in colored reproductions of this type. Colors in the photographs may differ slightly from the color values cited in the detailed botanical description which accurately describe the colors of the new *Pieris* plant.

The photograph on the first sheet is a close-up view of typical developing leaves of 'Cabernet'.

The photograph on the second sheet is a close-up view of typical developed leaves and inflorescences of 'Cabernet'.

DETAILED BOTANICAL DESCRIPTION

The aforementioned photographs and following observations and measurements describe plants grown in ground beds in an outdoor nursery in Hopewell, Oreg. and under cultural practices typical of commercial production. Plants used for the photographs and description were eight years old. In the following description, color references are made to The Royal Horticultural Society Colour Chart, 2001 Edition, except where general terms of ordinary dictionary significance are used.

Botanical classification: *Pieris japonica* 'Cabernet'.

Parentage:

*Female, or seed, parent.*—*Pieris japonica* 'Reversal', not patented.

*Male, or pollen, parent.*—*Pieris japonica* 'Valley Valentine', not patented.

Propagation:

*Type.*—By stem cuttings.

*Time to initiate roots, autumn and winter.*—About nine weeks at temperatures about 20° C.

*Root description.*—Fine, fibrous; white to light brown in color.

*Rooting habit.*—Moderate branching; medium density.

Plant description:

*Plant and growth habit.*—Woody perennial, evergreen; compact, upright to outwardly spreading plant habit; oval to round in overall shape; moderately vigorous growth habit.

*Branching habit.*—Freely branching habit with typically about three to four lateral branches bypassing each terminal inflorescence; if terminal inflorescences removed, up to six lateral branches will develop.

*Plant height, soil level to top of flowers.*—About 160 cm.

*Plant diameter, area of spread.*—About 150 cm.

*Lateral branch description.*—Length: About 6 cm to 9 cm. Diameter: About 2 mm to 4 mm. Internode length: About 2 mm to 5 mm. Strength: Strong. Texture: Smooth, glabrous. Color: Close to between 144B and 144C.

*Leaf description.*—Arrangement: Whorled at terminals; simple. Length: About 6 cm to 9 cm. Width: About 1.8 cm to 2.5 cm. Shape: Elliptic to obelliptic. Apex: Acute. Base: Attenuate. Margin: Towards the base, entire; towards the apex, crenate. Venation pattern: Pinnate. Texture, upper and lower surfaces.—Smooth, glabrous. Color: Developing leaves, upper and lower surfaces: Close to between 180A and 180B. Fully expanded leaves, upper surface: Close to between 141A and 143A; venation, close to 144C to 144D. Fully expanded leaves, lower surface: Close to between 144A and 144B; venation, close to 144C. Petioles: Length: About 7 mm to 10 mm. Diameter: About 1 mm to 3 mm. Texture, upper and lower surfaces: Smooth, glabrous. Color, upper surface: Close to 181B and 144B. Color, lower surface: Close to 144B.

Flower description:

*Flower arrangement and appearance.*—Single urceolate flowers arranged in terminal paniculate racemes; developing inflorescences initially upright, then becoming more horizontal and then bending downwardly with the increasing weight of developing flowers.

*Flowering habit.*—Freely flowering habit; about 120 to 220 flowers develop per inflorescence during the flowering period.

*Natural flowering season.*—Relatively late flowering response; plants of the new *Pieris* typically flower from early March to early April in Hopewell, Oreg.

*Flower longevity.*—Individual flowers last about 12 to 28 days on the plant.

*Fragrance.*—Sweet, pleasant.

*Inflorescence length.*—About 12 cm to 24 cm.

*Inflorescence diameter.*—About 12 cm to 18 cm.

*Flower diameter.*—About 5 mm to 8 mm.

*Flower depth.*—About 8 mm to 10 mm.

*Flower buds.*—Length: About 5 mm to 7 mm. Diameter: About 3 mm to 5 mm. Shape: Ovoid. Color: Close to between N186D and 187A.

*Petals.*—Arrangement: Single urceolate flower form; single whorl of five petals fused at the base. Length: About 7 mm. Width: About 2 mm. Shape: Ovate with obtuse apex. Margin: Entire. Texture, upper and lower surfaces: Smooth, glabrous. Color: When opening, upper and lower surfaces: Close to between N186D and 187A. Fully opened, upper and lower surfaces: Close to 71A and becoming closer to 71C to 71D with development; towards the base, close to 155C to 155D.

*Sepals.*—Arrangement: Five fused in a single whorl. Length: About 2 mm to 4 mm. Width: About 1 mm to 2 mm. Shape: Ovate. Apex: Acute. Base: Cuneate to broadly cuneate. Texture, upper and lower surfaces: Smooth, glabrous. Color: Immature, upper and lower surfaces: Close to 71A. Mature, upper and lower surfaces: Close to 60B; towards the apex, fading to close to 155A.

*Peduncles.*—Length: About 8 cm to 12 cm. Diameter: About 1 mm to 2 mm. Angle: Initially upright to about 80° from vertical. Strength: Moderately strong. Texture: Smooth, glabrous. Color: Close to 71A.

*Pedicels.*—Length: About 3 mm to 6 mm. Diameter: About 1 mm to 2 mm. Angle: About 40° to 60° from vertical. Strength: Moderately strong. Texture: Smooth, glabrous. Color: Close to 71A.

*Reproductive organs.*—Androecium: Quantity per flower: About ten. Anther shape: Oval. Anther length: About 1 mm. Anther color: Close to 200A. Pollen amount: Scarce. Pollen color: Close to 167C. Gynoecium: Quantity of pistils per flower: Typically one. Pistil length: About 4 mm to 6 mm. Style length: About 4 mm to 5 mm. Style color: Close to 145C to 145D. Stigma shape: Narrowly club-shaped. Stigma diameter: Less than 1 mm. Stigma color: Close to 145C. Ovary color: Close to 145C.

*Seeds and fruits.*—Seed and fruit development have not been observed on plants of the new *Pieris.*

Garden performance: Plants of the new *Pieris* have been observed to have good garden performance and to be tolerant to rain, wind, ice to 1.5 cm in thickness, snow to 8 cm in thickness and temperatures from about −19° C. to about 42° C.

Disease & pest resistance: Plants have not been observed to be resistant to pathogens and pests common to *Pieris* plants.

It is claimed:

1. A new and distinct cultivar of *Pieris* plant named 'Cabernet' as illustrated and described.

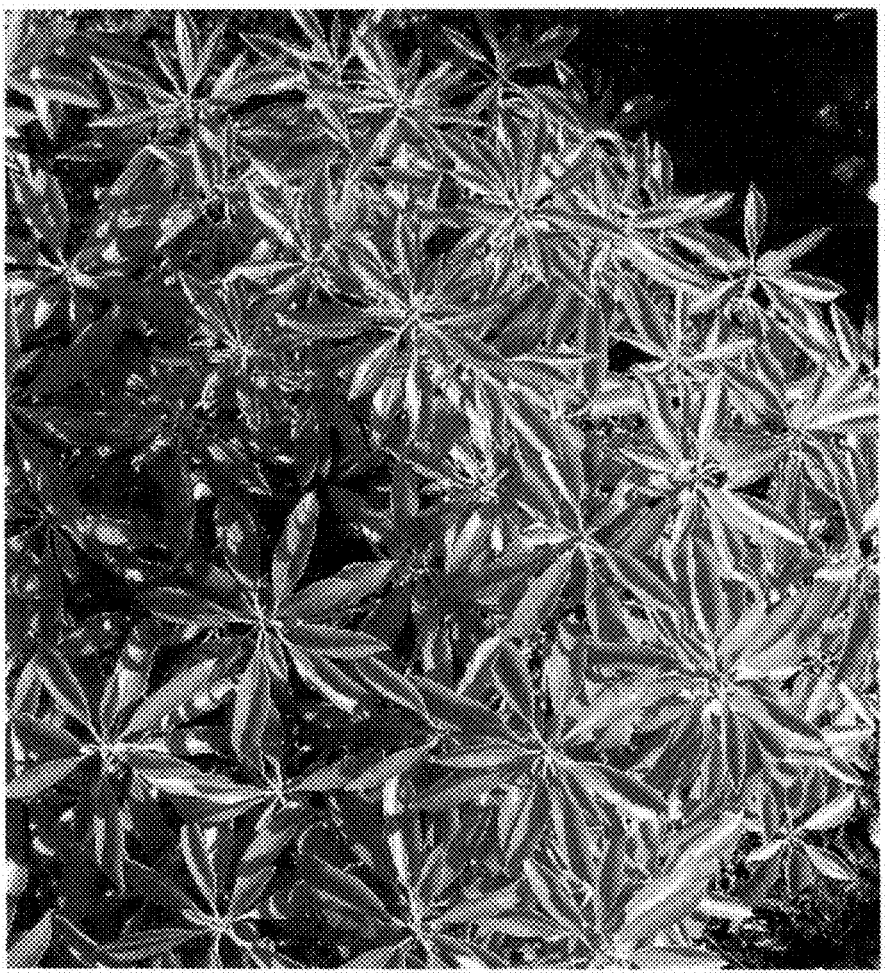

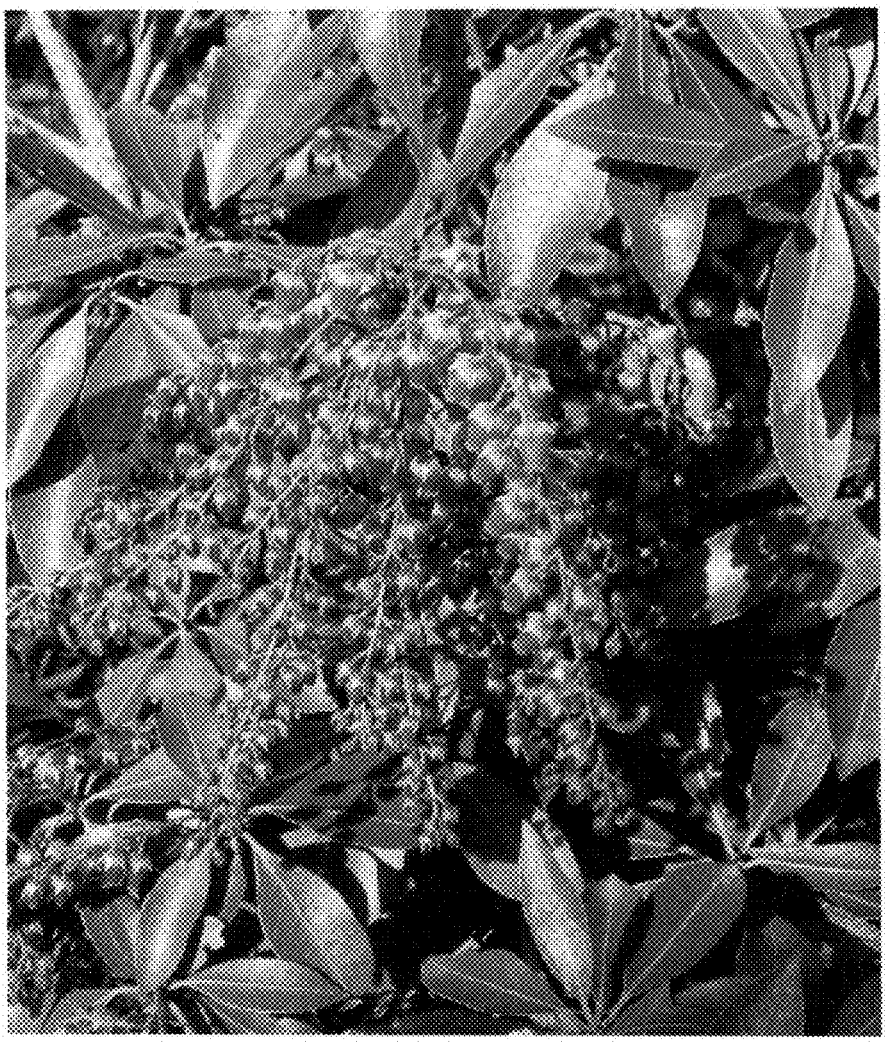

* * * * *